United States Patent
Kang et al.

(10) Patent No.: US 12,325,867 B2
(45) Date of Patent: *Jun. 10, 2025

(54) ORGANOID PRODUCED USING CARRIER FOR CELL CULTURE, AND METHOD FOR EVALUATING DRUG TOXICITY USING SAME

(71) Applicant: Korea Research Institute of Chemical Technology, Daejeon (KR)

(72) Inventors: Sun Woong Kang, Daejeon (KR); Hye Eun Shim, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 474 days.

This patent is subject to a terminal disclaimer.

(21) Appl. No.: 17/283,516

(22) PCT Filed: Nov. 12, 2019

(86) PCT No.: PCT/KR2019/095042
§ 371 (c)(1),
(2) Date: Apr. 7, 2021

(87) PCT Pub. No.: WO2020/101461
PCT Pub. Date: May 22, 2020

(65) Prior Publication Data
US 2021/0388313 A1    Dec. 16, 2021

(30) Foreign Application Priority Data
Nov. 13, 2018   (KR) .................. 10-2018-0139220

(51) Int. Cl.
*C12N 5/00* (2006.01)
*G01N 33/50* (2006.01)

(52) U.S. Cl.
CPC ....... *C12N 5/0075* (2013.01); *G01N 33/5014* (2013.01); *C12N 2500/76* (2013.01); *C12N 2531/00* (2013.01); *C12N 2533/54* (2013.01); *C12N 2533/80* (2013.01)

(58) Field of Classification Search
CPC ............. C12N 5/0075; C12N 2500/76; C12N 2531/00; C12N 2533/54; C12N 2533/80; G01N 33/5014
See application file for complete search history.

(56) References Cited

U.S. PATENT DOCUMENTS

| 5,051,304 | A |   | 9/1991  | David et al. |
| 5,693,343 | A |   | 12/1997 | Reid et al. |
| 7,255,874 | B1 | * | 8/2007 | Bobo .................. A61L 27/34 424/450 |
| 8,557,288 | B2 | * | 10/2013 | Elbert .................. A61L 27/52 424/94.1 |
| 11,077,032 | B2 |  | 8/2021 | Goutayer |
| 11,160,761 | B2 |  | 11/2021 | Brahms |
| 2007/0042184 | A1 |  | 2/2007 | Coyne |
| 2009/0087569 | A1 |  | 4/2009 | Fan |
| 2012/0076839 | A1 |  | 3/2012 | Chan |
| 2012/0269748 | A1 |  | 10/2012 | Tamura |
| 2014/0349396 | A1 | * | 11/2014 | West ................ C12N 5/069 435/325 |
| 2016/0083690 | A1 |  | 3/2016 | Birch |

FOREIGN PATENT DOCUMENTS

| CN | 1485094 A | * | 3/2004 |
| CN | 1641017 A |  | 7/2005 |
| CN | 102952274 B |  | 3/2013 |
| JP | 2007-215519 |  | 8/2007 |
| KR | 10-0871-6520000 |  | 12/2008 |
| KR | 10-2012-0089329 B1 |  | 8/2012 |
| KR | 10-2013-0138240 B1 |  | 12/2013 |
| KR | 10-2014-0126972 A |  | 3/2014 |
| KR | 10-2016-0077757 A |  | 7/2016 |
| KR | 10-1655-4070000 |  | 9/2016 |
| KR | 10-2016-013778 |  | 12/2016 |
| WO | 2015-173425 A1 |  | 11/2015 |

OTHER PUBLICATIONS

Karmakar, G., et al. "Chemically modifying vegetable oils to prepare green lubricants," Lubricants 5(4): 44. (Year: 2017).*
Antonov, S. A., et al., "The Current State of Development of Greases," Chemistry and Technology of Fuels and Oils 57(2): 279-288. (Year: 2021).*
Martin-Alfonso, M. A., et al. "Impact of vegetable oil type on the rheological and tribological behavior of Montmorillonite-Based oleogels." Gels 8(8): 504. (Year: 2022).*
Mousa, M., et al., "Clay nanoparticles for regenerative medicine and biomaterial design: A review of clay bioactivity," Biomaterials 159: 204-214. doi: 10.1016/j.biomaterials.2017.12.024. Epub Jan. 3, 2018. (Year: 2018).*

(Continued)

*Primary Examiner* — Tracy Vivlemore
*Assistant Examiner* — Eric J Rogers
(74) *Attorney, Agent, or Firm* — Barry L. Davison; Davis Wright Tremaine LLP

(57) ABSTRACT

The present invention relates to an organoid and, more specifically, to an organoid and a use thereof, the organoid being produced using a carrier for cell culture which comprises microcapsules containing gelatin, a natural polymer, an oil, and an oil thickener. When used as a carrier for cell culture in culturing cells, the microcapsules containing a natural oil, according to the present invention, have the effects of improving adhesion and survival of the cells and inducing maturation of the cultured cells. The organoid produced by culturing cells using the carrier for cell culture has been confirmed to have the function of the organ concerned and, when treated with a drug, react to the toxicity of the drug and thus may be variously employed in the development of new drugs, disease research, and the field of artificial organ development.

7 Claims, 16 Drawing Sheets

(56) References Cited

OTHER PUBLICATIONS

Tuveson, D., and Clevers, H., "Cancer modeling meets human organoid technology," Science 364: 952-955. doi: 10.1126/science.aaw6985. (Year: 2019).*

Yamaguchi, M., ed., *Drosophila* models for human diseases. Springer; Jun. 27, 2018. (Year: 2018).*

Xiong, R., et al., "Naturally-derived biopolymer nanocomposites: Interfacial design, properties and emerging applications," Materials Science and Engineering: R: Reports 125: 1-41. (Year: 2018).*

Jensen, C., and Teng, Y., "Is It Time to Start Transitioning From 2D to 3D Cell Culture?," Front Mol Biosci 7: 33. doi: 10.3389/fmolb.2020.00033. (Year: 2020).*

Suflita, M., et al., "Heparin and related polysaccharides: synthesis using recombinant enzymes and metabolic engineering," Appl Microbiol Biotechnol 99(18): 7465-7479. doi: 10.1007/s00253-015-6821-9. (Year: 2015).*

Sato, N., et al., "Lipid metabolism and potentials of biofuel and high added-value oil production in red algae," World J Microbiol Biotechnol 33(4): 74. doi: 10.1007/s11274-017-2236-3. (Year: 2017).*

Campas, O., et al., "Quantifying cell-generated mechanical forces within living embryonic tissues," Nat Methods 11(2): 183-189. doi: 10.1038/nmeth.2761. Dec. 8, 2013. (Year: 2013).*

Gonçalves, N. D., et al., "Comparison of microparticles produced with combinations of gelatin, chitosan and gum Arabic," Carbohydr Polym 196: 427-432. doi: 10.1016/j.carbpol.2018.05.027. Epub May 9, 2018. (Year: 2018).*

Nirmala, D., et al. "Gelatin and Gelatin-Polyelectrolyte Complexes: Drug Deliver," Research Gate <https://www.researchgate.net/publication/293763161, Jan. 2016, pp. 3557-3569.

Shim, J.-K., "Three-Dimensional Co-Culture of Cells Using the Iron Oxide Containing Silk Fibroin Microcapsules Based on Magnetic Levitation," Department of Bioengineering and Technology, Graduate School, Kangwon National University, Feb. 2017, 86 pages.

International Search Report dated Mar. 4, 2020, issued in International Patent Application No. PCT/KR2019/095042, filed Nov. 12, 2019, 4 pages.

Arancibia, C., et al., "Application of CMC as Thickener on Nanoemulsions Based on Olive Oil: Physical Properties and Stability," International Journal of Polymer Science 2016: 1-10, Article ID 6280581, Oct. 18, 2016.

Marques Da Silva, T., et al., "Development and Characterization of Microcapsules Containing Bifidobacterium Bb-12 Produced by Complex Coacervation Followed by Freeze Drying," LWT—Food Science and Technology 90:412-417, 2018.

McLain, V.C., "Final Report of the Cosmetic Ingredient Review Expert Panel on the Safety Assessment of Polyisobutene and Hydrogenated Polyisobutene as Used in Cosmetics," International Journal of Toxicology 27(Suppl. 4):83-106, 2008.

International Search Report dated Mar. 3, 2020, issued in International Patent Application No. PCT/KR2019/095041, filed Nov. 12, 2019, 4 pages.

International Search Report dated Feb. 25, 2020, issued in International Patent Application No. PCT/KR2019/015349, filed Nov. 12, 2019, 4 pages.

Gasperini, L., et al., "Natural Polymers of the Microencapsulation of Cells," Journal of the Royal Society Interface 11(100):1-19; Nov. 6, 2014.

\* cited by examiner

[Figure 1a]
A. Oil thickener non-added group
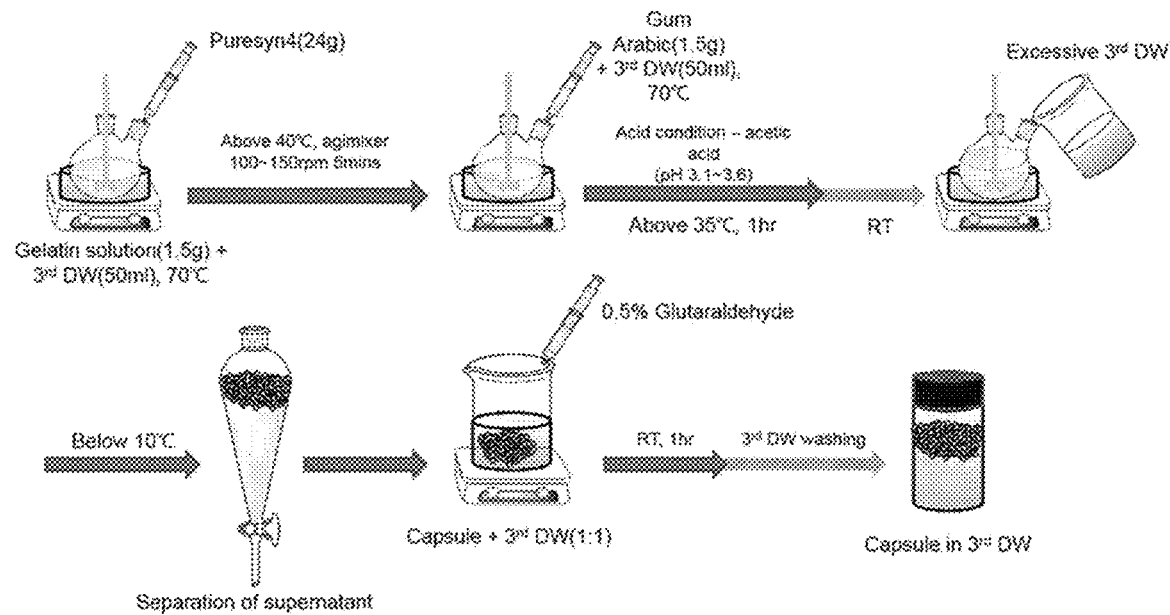
[Figure 1b]
B. Oil thickener added group
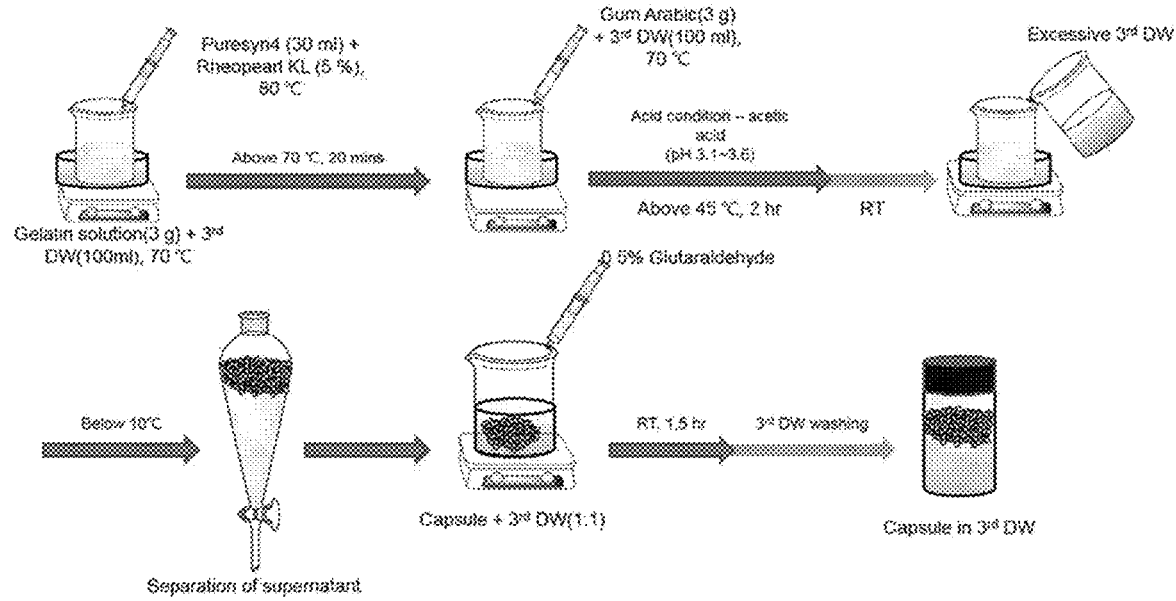

[Figure 2]
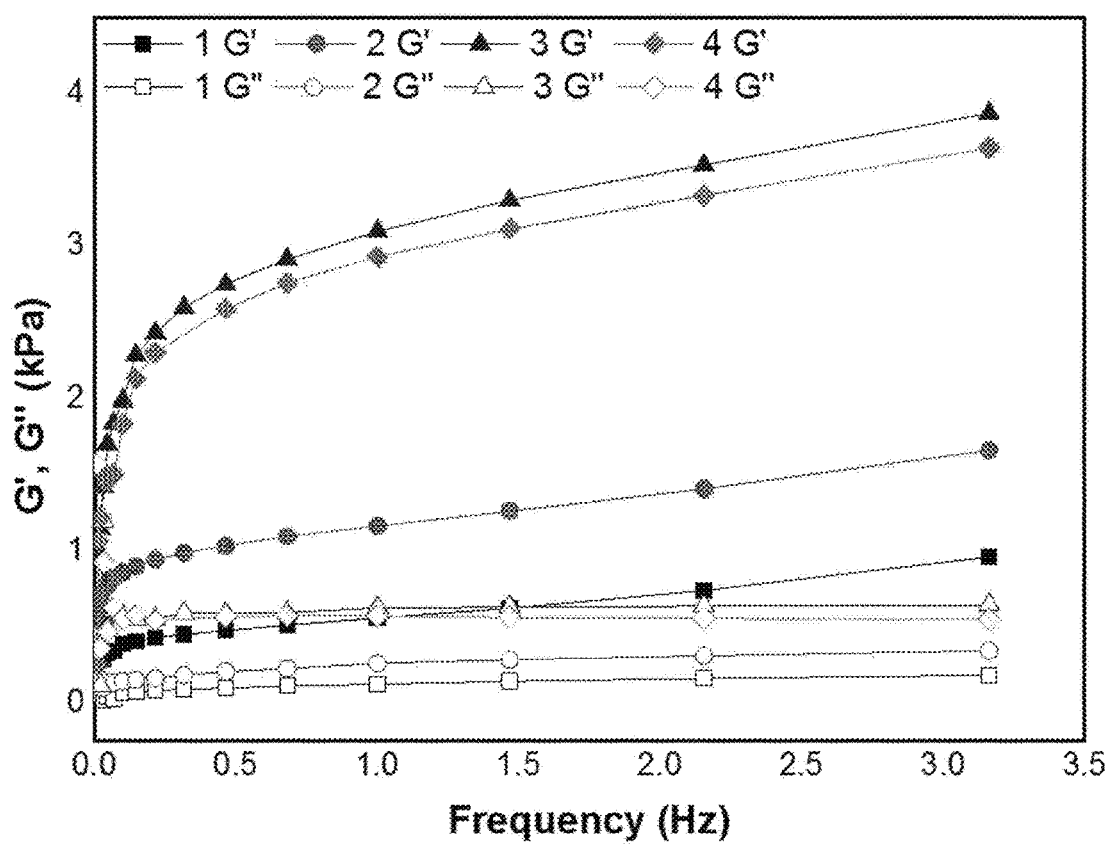
Mechanical properties. Frequency of 0.01 to 5 Hz, Strain of 0.01% at 24°C

[Figure 3]
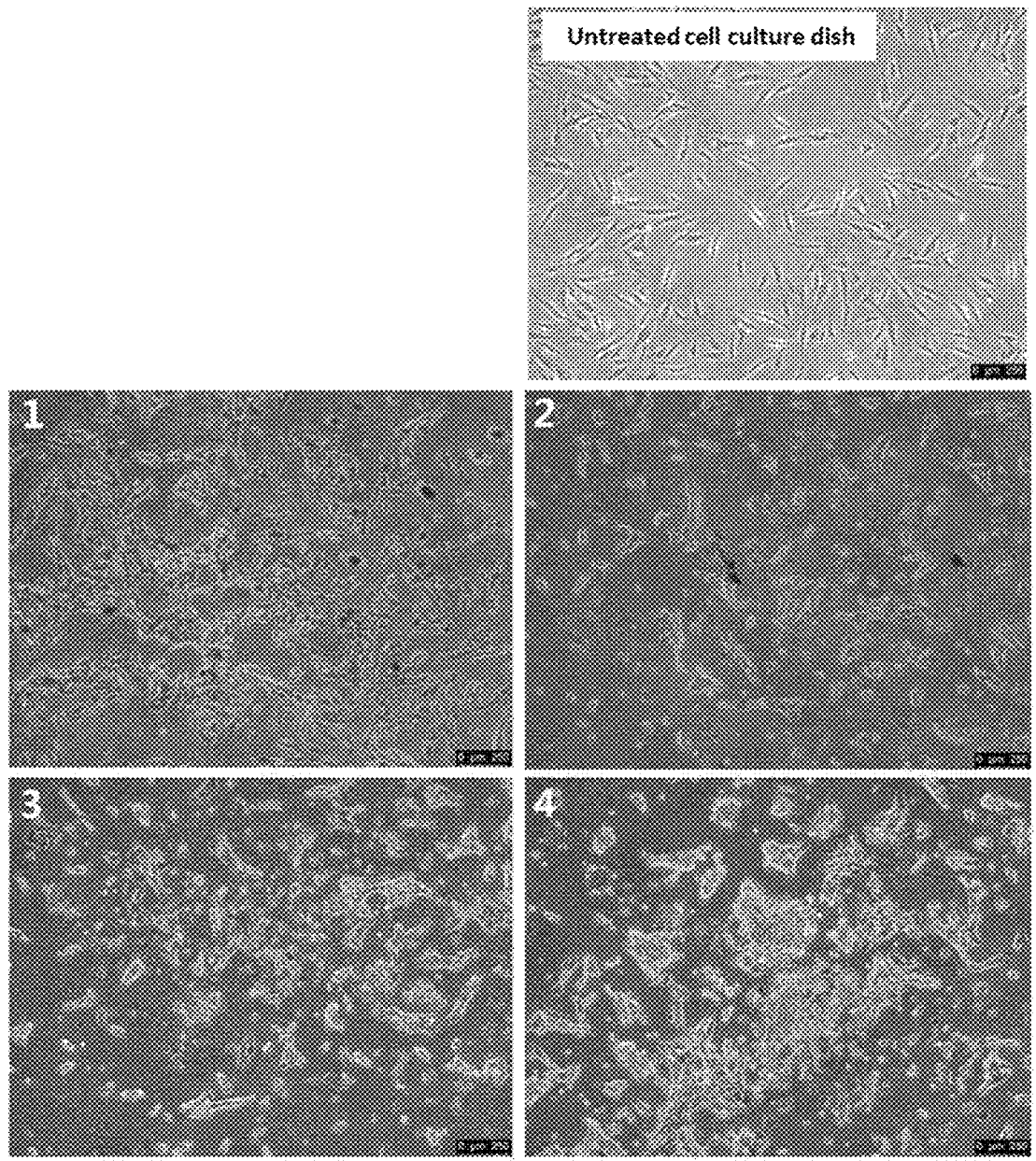

[Figure 4]
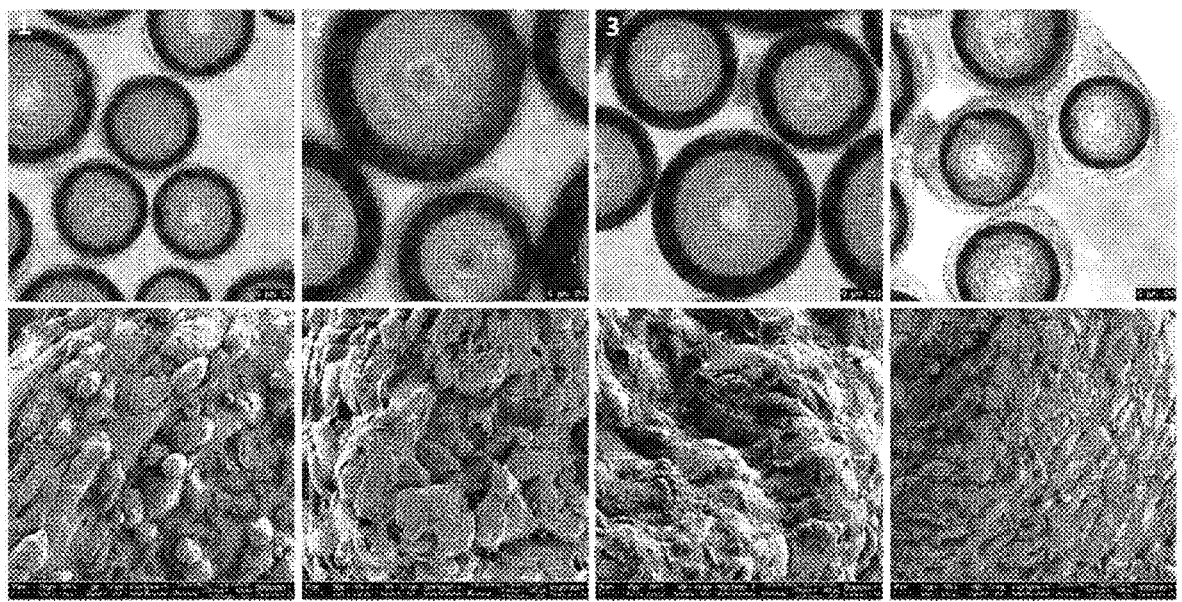

[Figure 5]
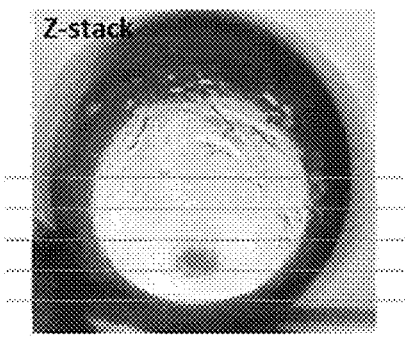
Checking cell viabilities of cardiomyocytes adhered to the surface of squalane through live-dead assay
(Z-stack, Confocal)
Green : Live, Red : Dead
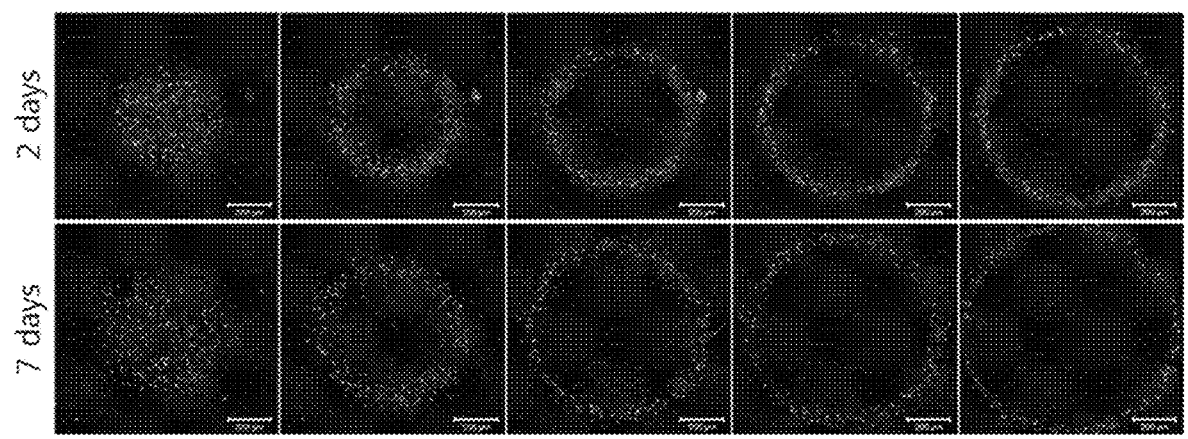

[Figure 6]
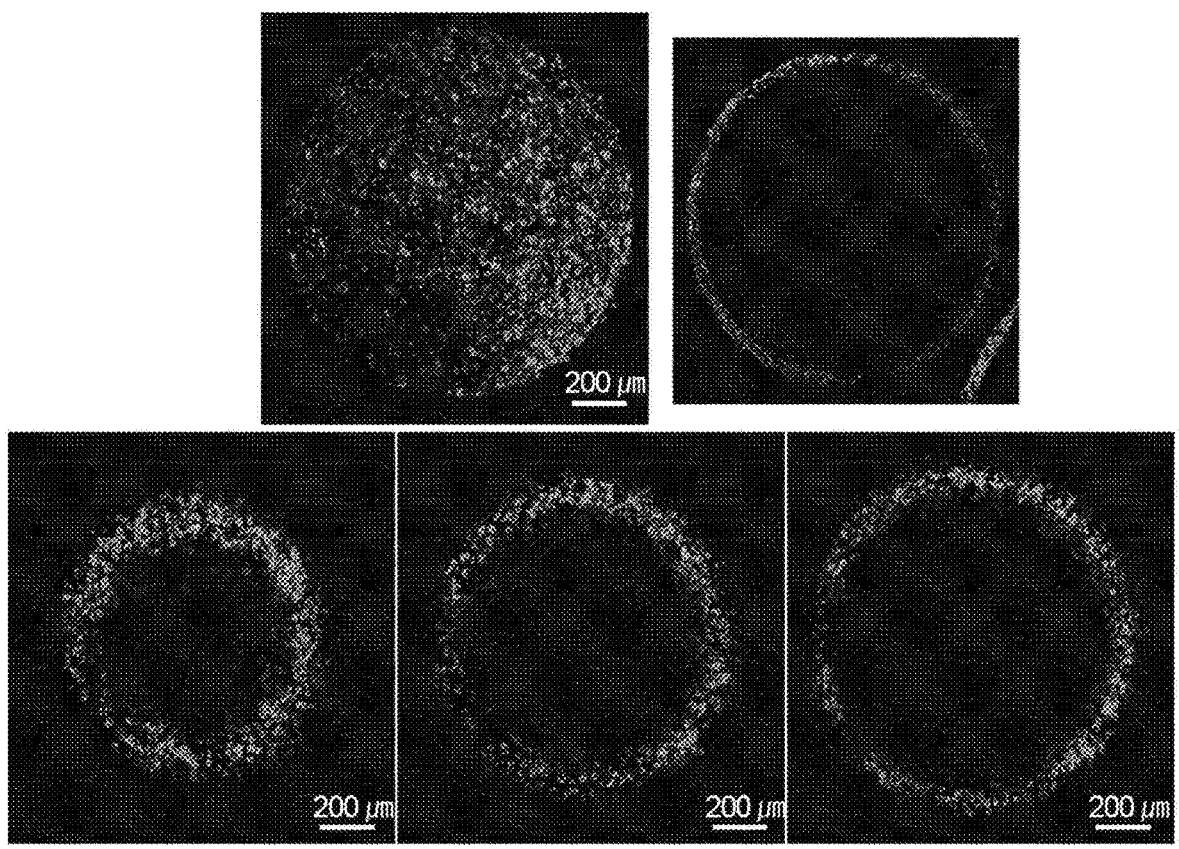

[Figure 7]
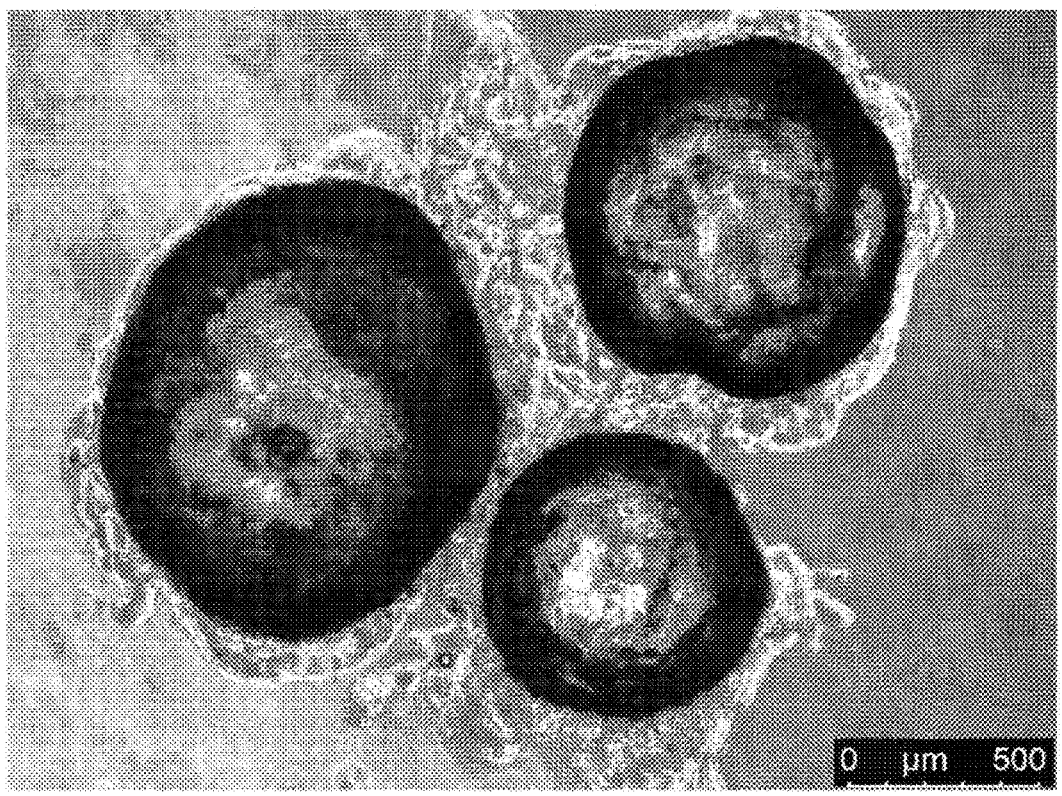

[Figure 8]
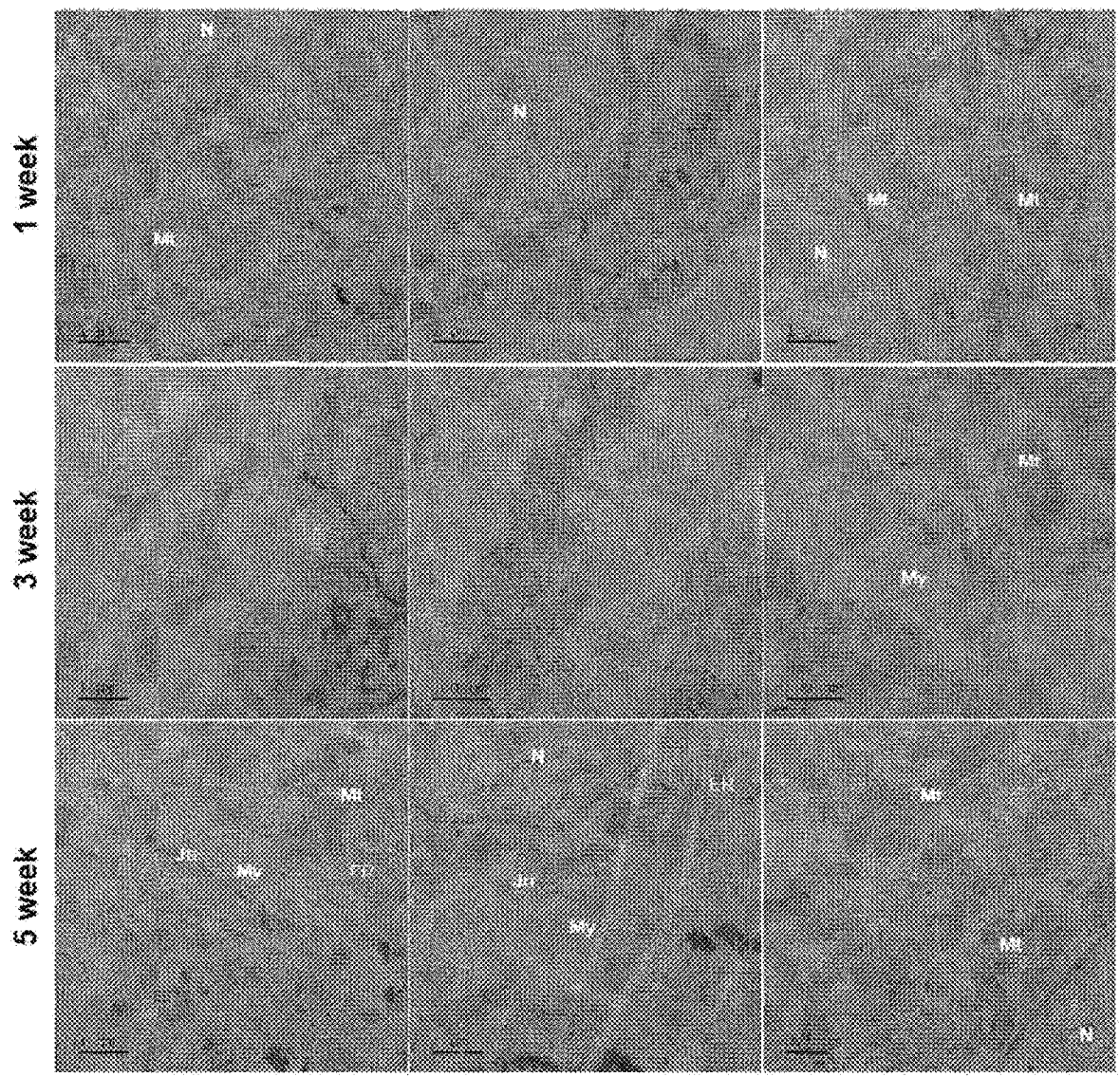

[Figure 9]
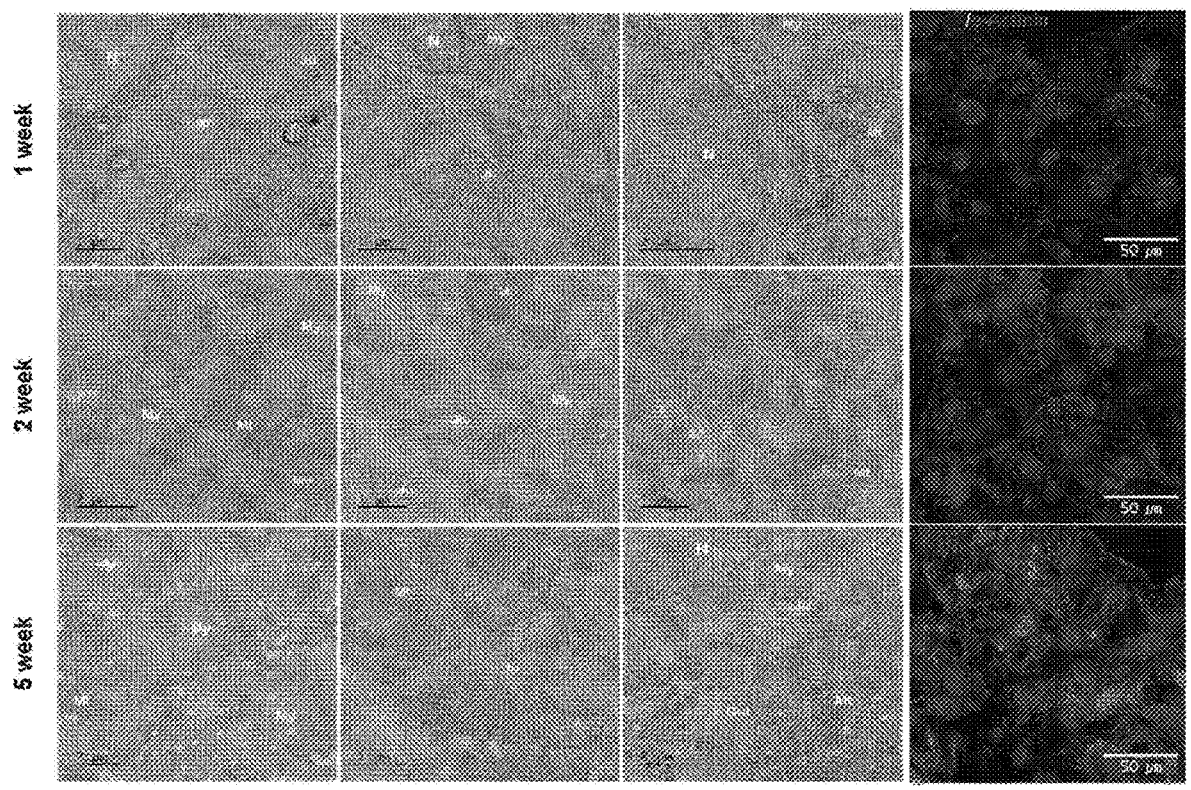

[Figure 10]
Experimental group 4 (Oil thickener untreated)
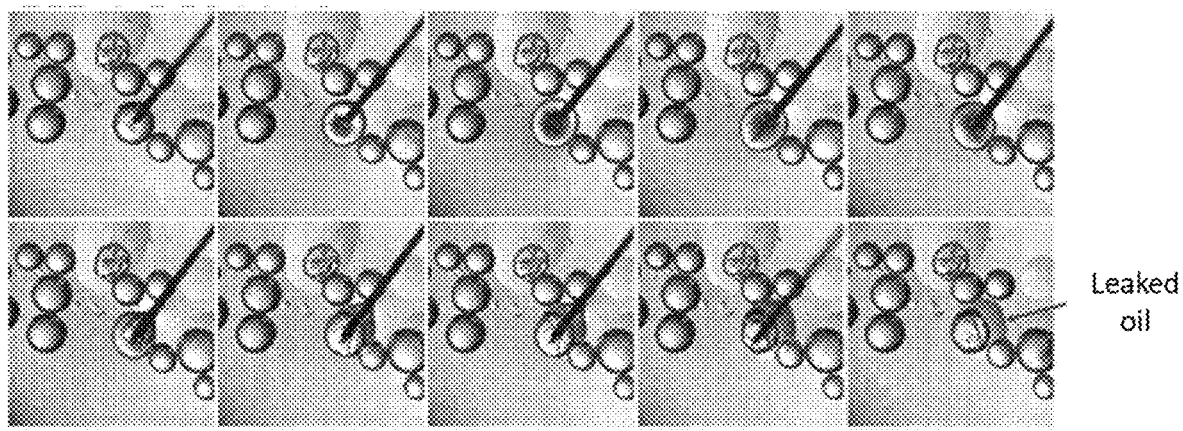
Leaked oil
Experimental group 10 (Oil thickener treated)
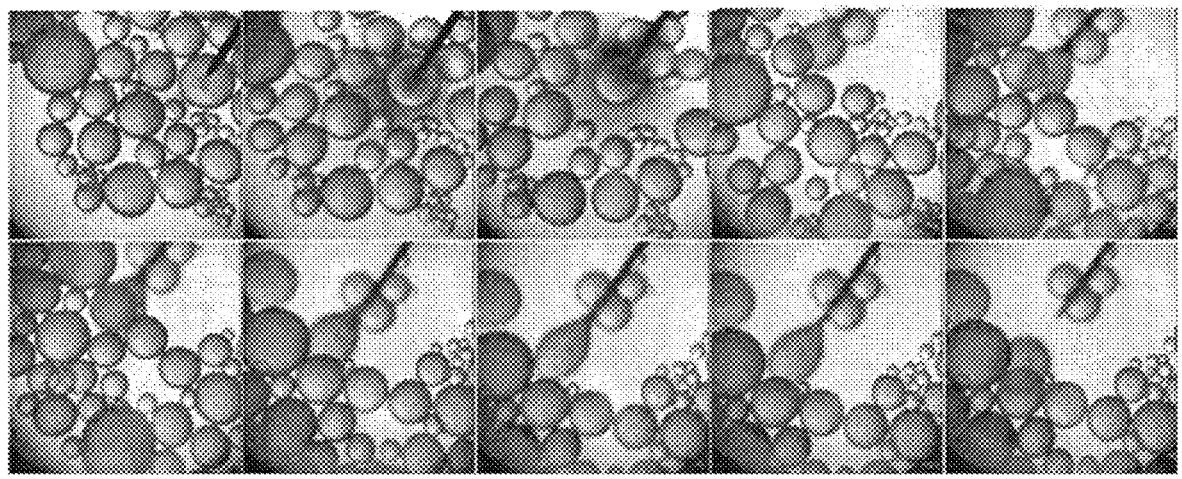

[Figure 11]
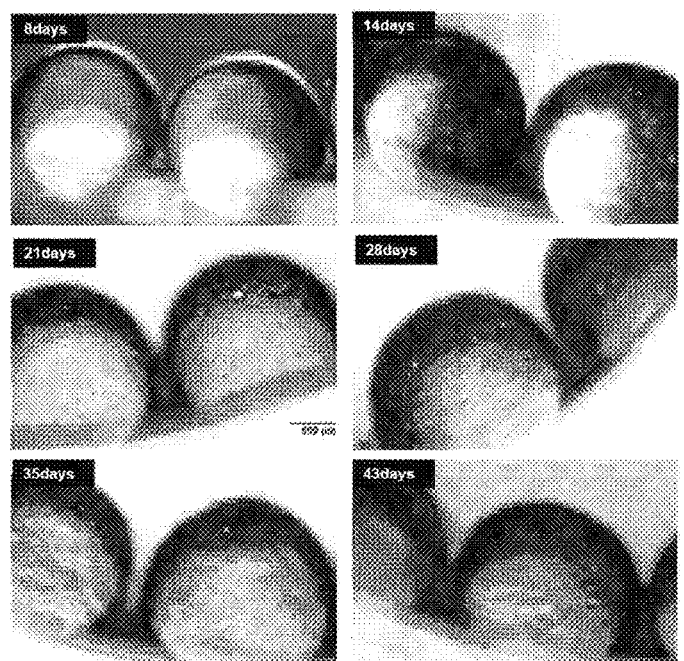
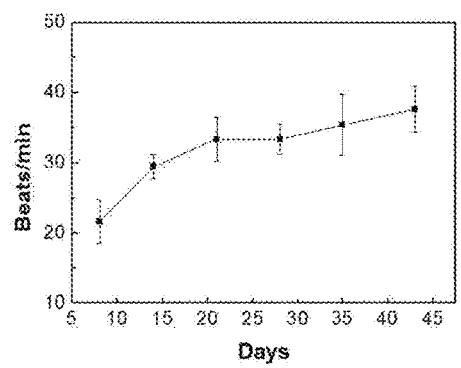
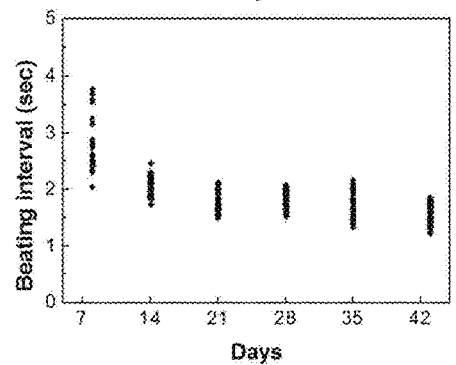

[Figure 12]
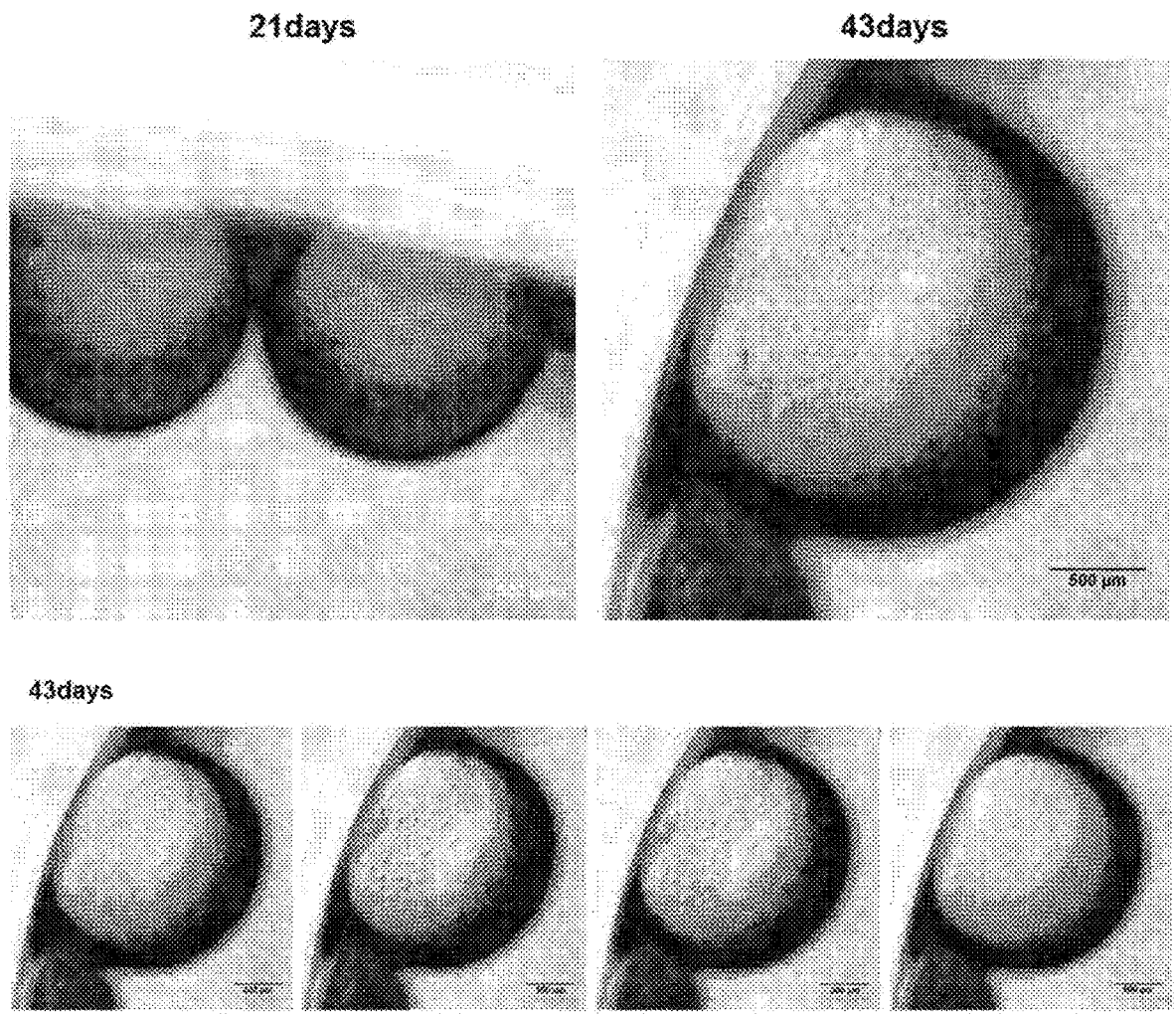

[Figure 13]
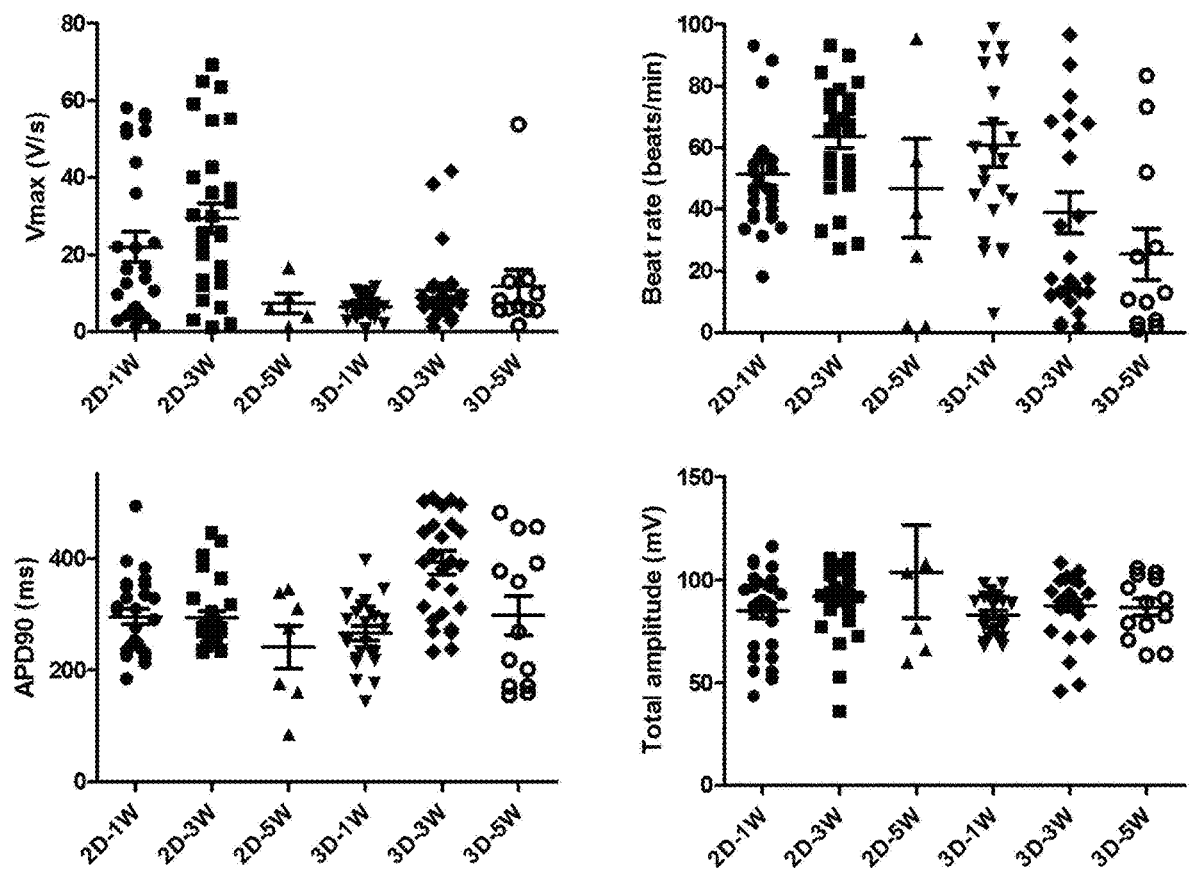

[Figure 14]
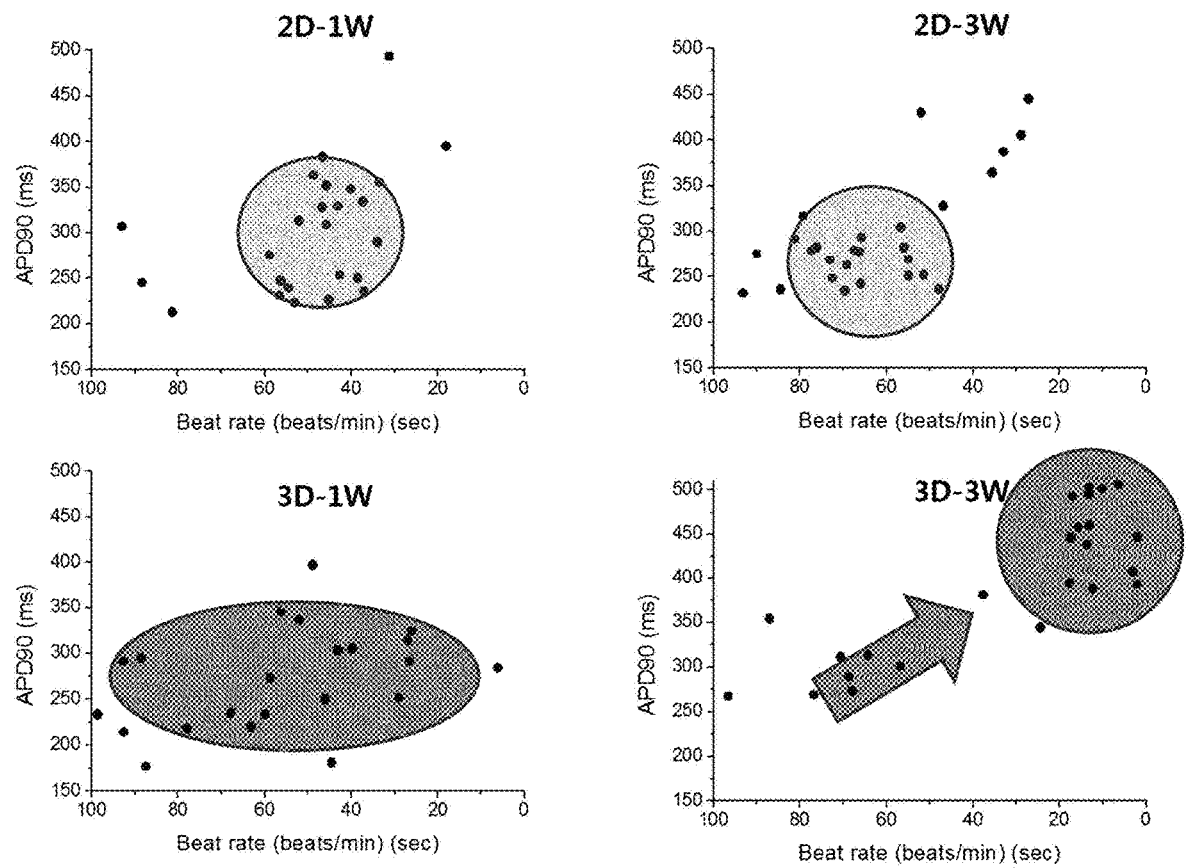

[Figure 15]
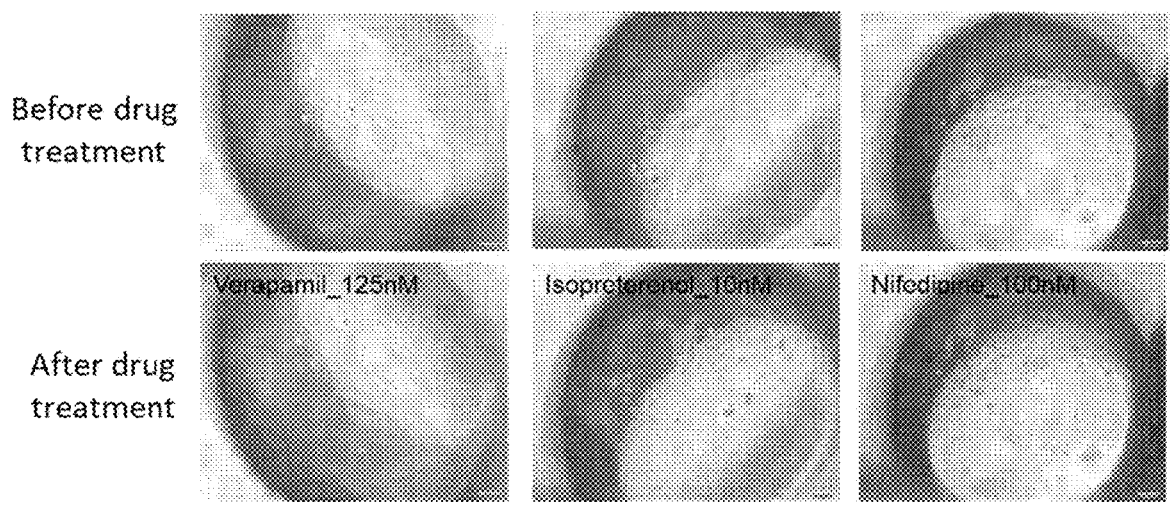

[Figure 16]
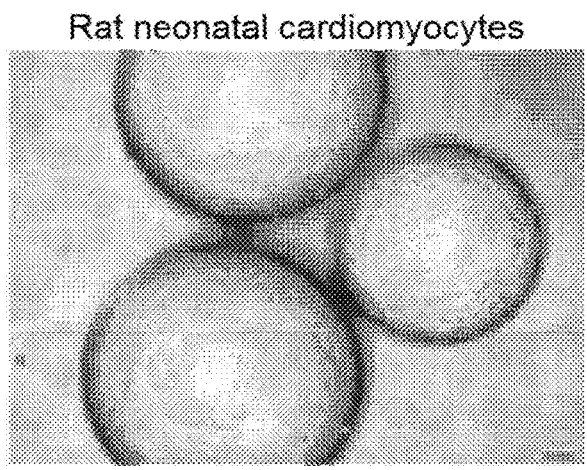
Rat neonatal cardiomyocytes
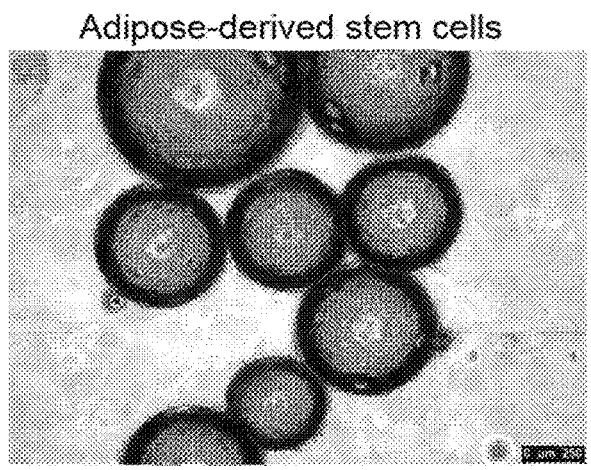
Adipose-derived stem cells
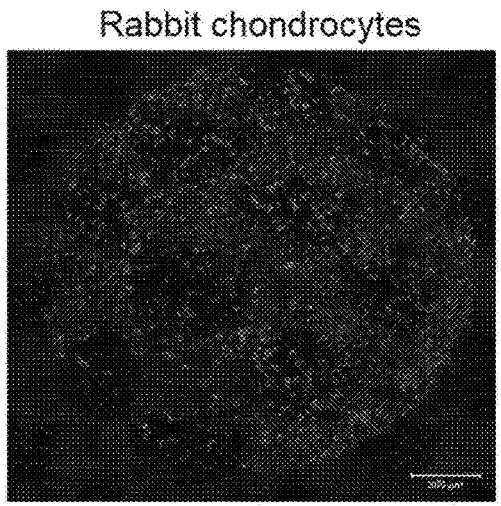
Rabbit chondrocytes
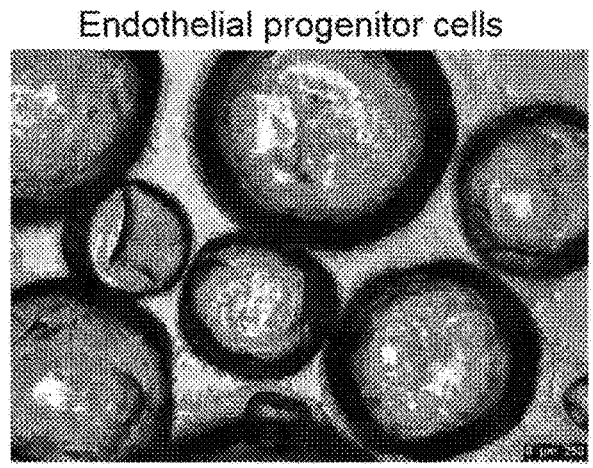
Endothelial progenitor cells

ORGANOID PRODUCED USING CARRIER FOR CELL CULTURE, AND METHOD FOR EVALUATING DRUG TOXICITY USING SAME

TECHNICAL FIELD

The present invention relates to an organoid, and more particularly, to an organoid and a use thereof, the organoid being produced using a carrier for cell culture which comprises microcapsules containing gelatin, a natural polymer, an oil, and an oil thickener.

BACKGROUND ART

Microcapsules mean ultrafine particles which have sizes of about several microns to hundreds of microns, and in which a liquid phase or solid phase material forming an inner part (core) is surrounded by a polymer material or the like forming an outer part (wall). Such microcapsules may be used in preventing the degeneration of a core material with respect to an external environment (for example, oxygen or moisture), constantly maintaining the transfer rate of material such as a sustained release drug or an air freshener, or converting a material used as the core from a liquid from to a solid form. The microcapsules, as a generic technology used in various fields such as medicine and medical supplies, paints, electronic industry, cosmetic products, etc., have been used as the best tool of maintaining the initial potency of the drug when the microcapsules are used especially in the medicine and medical supplies and the cosmetic products.

Meanwhile, it has been reported that a three-dimensional organoid is cultured in material such as Matrigel that mimics an extracellular matrix, and these three-dimensional culturing techniques have very few karyotypic changes and no spontaneous carcinogenesis differently from an existing two-dimensional cell culturing method. Accordingly, organoid culturing is considered advantageous in preserving characteristics of the body over the long term compared to any cell culturing method that has ever been presented up to now. Since recent three-dimensional organ mimicking organoids may become a disease mimicking model that is essential in the implementation of patient-tailored treatment as well as the basic study of disease understanding, the three-dimensional organ mimicking organoids are expected to be usefully applied in the field of precision medicine in the fixture. More specifically, the most efficient drugs may be applied to customized treatment by understanding characteristics of diseases with different properties by patients, and discovering the most efficient drugs using an organoid platform.

DISCLOSURE

Technical Problem

Accordingly, the present inventors have completed the present invention by developing an organoid by culturing cells together with microcapsules, and confirming that the organoid has the function of an organ concerned.

Therefore, an object of the present invention is to provide an organoid, a production method of the organoid, and a method of inspecting the activity or toxicity of a test material using the organoid.

Technical Solution

In order to achieve the aforementioned object, the present invention provides an organoid production method comprising the step of simultaneously culturing cells and a carrier for cell culture comprising microcapsules which contain gelatin, a natural polymer, an oil, and an oil thickener.

Furthermore, the present invention provides an organoid produced by the foregoing method.

Furthermore, the present invention provides a method of inspecting the activity or toxicity of a test material, the method comprising a step of treating the organoid with the test material and a step of measuring activity of the organoid.

Advantageous Effects

When used as a carrier for cell culture in culturing cells, microcapsules containing a natural oil, according to the present invention, have the effects of improving adhesion and survival of the cells and inducing maturation of the cultured cells. An organoid produced by culturing cells as the carrier for cell culture has been confirmed to have the function of the organ concerned and, when treated with a drug, react to the toxicity of the drug and thus may be diversely used in the development of new drugs, disease research, and the field of artificial organ development.

DESCRIPTION OF DRAWINGS

FIG. 1 illustrates a preparation method of gelatin oil capsules according to the present invention (A: when an oil thickener is not added, B: when the oil thickener is added).

FIG. 2 shows elastic modulus measurement results of gelatin oil capsules according to the present invention.

FIGS. 3 and 4 are views showing results of observing cultured cells through an optical microscope, a scanning electron microscope (SEM), and a transmission electron microscope (TEM) after coculturing gelatin oil capsules according to the present invention and cardiomyocytes.

FIG. 5 is a view showing results of checking the cellular viability of cardiomyocytes cocultured with gelatin oil capsules according to the present invention through live-dead assay.

FIG. 6 is a view showing results of observing cocultured cells through a confocal microscope after coculturing gelatin oil capsules according to the present invention and cardiomyocytes differentiated from mesenchymal stem cells.

FIG. 7 is a view showing results of observing cocultured cells through a microscope after coculturing gelatin oil capsules according to the present invention and HeLa cells.

FIG. 8 is a view showing results of observing, through a TEM, results of culturing cardiomyocytes by a conventional method.

FIG. 9 is a view showing results of observing, through a TEM and a fluorescence microscope, results of coculturing gelatin oil capsules according to the present invention and cardiomyocytes.

FIG. 10 is a view showing results of comparing retention degrees of gelatin oil capsules according to the present invention depending on whether an oil thickener has been added or not.

FIGS. 11 and 12 are views showing results of checking beat rates and beating intervals of an artificial myocardial structure according to the present invention.

FIGS. 13 and 14 are views showing results of verifying functions of an artificial myocardial structure according to the present invention.

FIG. 15 is a view showing results of the contractile force-based cardiac toxicity assessment using an artificial myocardial structure according to the present invention.

FIG. 16 is a view showing results of coculturing gelatin oil capsules according to the present invention and various cells.

MODES OF THE INVENTION

Hereinafter, the present invention will be described in detail.

According to an aspect of the present invention, the present invention provides an organoid production method comprising the step of simultaneously culturing cells and a carrier for cell culture comprising microcapsules which contain gelatin, a natural polymer, an oil, and an oil thickener.

In the present invention, a "carrier" means particles useful in adhesion and growth of anchorage-dependent cells, and the carrier may be about 10 to 800 μm, i.e., a size that is small enough to be used in suspension culture, and the carrier is not limited thereto.

In the present invention, a "natural polymer" means a polymer material which is present in nature or produced by living things, and the natural polymer plays roles of oxidation prevention and stabilization of oil inside microcapsules.

Although examples of the natural polymer may include Arabic gum, hyaluronic acid, guar gum, pectin, xanthan gum, locust bean gum, tamarind gum, tragacanth gum, gum ghatti, locust bean gum, Konjac gum, agar, Carragheenan, furcellaran, gellan, etc., the natural polymer is not limited thereto.

In an embodiment of the present invention, the gelatin and the natural polymer are preferably mixed at a weight ratio of 1:0.1 to 1.

According to a preferred embodiment of the present invention, the natural polymer is preferably Arabic gum, more preferably a mixture of Arabic gum and hyaluronic acid, and Arabic gum and hyaluronic acid are more preferably mixed at a weight ratio of 1:9 to 9:1 in the mixture of Arabic gum and hyaluronic acid.

In the present invention, the oil may be one or more selected from the group consisting of olive oil, camellia oil, castor oil, palm oil, Jojoba oil, almond oil, grapeseed oil, herbal oil, rose oil, coconut oil, moringa oil, rice bran oil, apricot kernel oil, sunflower oil, meadowfoam seed oil, Abyssinian oil, and squalane, and is not limited thereto. In an embodiment of the present invention, the oil is preferably squalane. The squalane may be phytosqualane.

In the present invention, "Phytosqualane", as a natural squalane replacing animal squalane, is produced by adding hydrogen to squalane extracted from vegetable oil. Phytosqualane has a function of preventing evaporation of moisture, and microcapsules prepared by adding phytosqualane have the advantage of maintaining moisture in the capsules for a long time.

In the present invention, a "thickener", as a material of increasing the viscosity of a solution, is referred to as a thickener or a thickening stabilizer. In addition, since the solution appears to be sticky when adding the thickener to the solution, there is a case that the thickener is written as a thickening agent as it seems as if the solution is concentrated. In the present invention, the thickener has been used in order to improve the viscosity of an oil contained inside microcapsules.

In an embodiment of the present invention, the oil thickener may be one or more selected from Bentone gel® (disteardimonium hectorite), hydrogenated polyisobutene, dextrin palmitate/ethylhexanoate, and dextrin palmitate, and may be more preferably dextrin palmitate. The oil thickener may also be one or more selected from Bentone gel®, Versagel® ME 750 (hydrogenated polyisobutene), Rheopearl® TT (dextrin palmitate/ethylhexanoate), and Rheopearl® KL (dextrin palmitate) that are commercially available.

In the present invention, although the oil thickener may be contained in an amount of 1 to 15 wt %, preferably 2 to 10 wt %, more preferably 4 to 6 wt %, and most preferably 5 wt % with respect to the weight of the oil, the content of the oil thickener is not limited thereto.

In another embodiment of the present invention, the microcapsules are preferably prepared by a preparation method shown in FIG. 1B. Specifically, the microcapsules comprises: a step (a) of preparing a gelatin solution containing gelatin, an oil, and an oil thickener; a step (b) of preparing a natural polymer solution; a step (c) of mixing the gelatin solution and the natural polymer solution; a step (d) of adjusting pH of a mixture prepared in the step (c); and a step (e) of cooling a pH-adjusted mixture.

Although the oil thickener of the step (a) may be contained in an amount of 1 to 15 wt %, preferably 2 to 10 wt %, more preferably 4 to 6 wt %, and most preferably 5 wt % with respect to the weight of the oil, the content of the oil thickener is not limited thereto.

Although the natural polymer solution of the step (b) is preferably a mixture obtained by mixing Arabic gum and hyaluronic acid at a weight ratio of 1:9 to 9:1, the natural polymer solution is not limited thereto.

The step (d) preferably comprises adjusting pH of the mixture of the gelatin solution and the natural polymer solution to 3.1 to 3.6.

Furthermore, the step (e) preferably comprises adding distilled water corresponding to 3 to 5 times the pH-adjusted mixture to the pH-adjusted mixture, stirring the distilled water in the pH-adjusted mixture, and cooling the stirred material so that temperature of a stirred material becomes 5° C. to 15° C.

In an embodiment of the present invention, although the cells are preferably anchorage-dependent cells, and more preferably one or more selected from the group consisting of cardiomyocytes, vascular endothelial cells, lipocytes, epithelial cells, fibroblasts, osteoblasts, chondrocytes, hepatocytes, uterine cervical cells, cancer cells, and mesenchymal stem cells, the cells are not limited thereto.

The mesenchymal stem cells may be derived from bone marrow, fat, cord blood, amniotic fluid, or amnion, and are not limited thereto.

The cancer cells mean all types of cancer derived cells. For example, although the cancer may include stomach cancer, colon cancer, breast cancer, lung cancer, liver cancer, bone cancer, pancreatic cancer, skin cancer, head or neck cancer, melanoma in the skin or eyeglobe, uterine cancer, ovarian cancer, colorectal cancer, small bowel cancer, rectal cancer, cancer nearby an anus, fallopian tube cancer, endometrial carcinoma, cervical carcinoma, vaginal carcinoma, vulvar carcinoma, esophageal cancer, small bowel cancer, lymphatic carcinoma, bladder cancer, gallbladder cancer, Endocrine adenocarcinoma, thyroid cancer, parathyroid cancer, adrenal cancer, soft tissue sarcoma, urethral cancer, penis cancer, prostate cancer, bladder cancer, renal or ureter cancer, brain cancer, etc., the cancer is not limited thereto.

In the present invention, "cell culture" refers to culturing of cells separated from the tissues of living organisms, and the type of medium, temperature conditions, culture solution, and the like follow the publicly-known method depending on the type of the cells.

According to other aspect of the present invention, the present invention provides an organoid produced by the foregoing method.

In the present invention, an "organoid" means a three-dimensional cell structure produced by three-dimensionally culturing or recombining cells, and is referred to as "a mini organ" or "a similar organ". The organoid specifically comprises one or more types of cells among various types of cells composing the organ or tissue, and should reproduce form and function of the tissue or organ.

The organoid may be used in new drug development, disease treatment, and artificial organ development. As the side effects that have not been found in animal testing are found in humans in existing drug tests when developing new drugs, the existing drug tests have limitations that results of the animal testing and clinical trials are different. The existing drug tests are not only expected to overcome these limitations through the organoid, but also may escape ethical controversy over the animal testing. Furthermore, a similar organ may be produced by culturing cells of a patient, the organoid is drawing attention as a methodology for personalized clinical trials; and may be used for personalized organ development and the like in the future.

Ali organoid according to the present invention, which is produced by culturing cells with a carrier for cell culture comprising microcapsules which contain gelatin, a natural polymer, an oil, and an oil thickener, has the function of an organ concerned and, when treated with a drug, reacts to the toxicity of the drug.

In an embodiment of the present invention, a cardiac organoid has been produced by simultaneously culturing cardiomyocytes and a carrier for cell culture at the same time. The produced cardiac organoid has characteristics of beating at regular intervals and reacting to a test material.

Types of the organoid may also vary depending on types of cells simultaneously cultured with a carrier for cell culture according to the present invention, and the organoid may be, for example, a cardiac organoid, a gastric organoid, a small intestinal organoid, a colonic organoid, a liver organoid, a thyroid organoid, a lung organoid, a brain organoid, or the like, and is not limited thereto.

According to another aspect of the present invention, the present invention provides a method of inspecting the activity or toxicity of a test material, the method comprising a step of treating the organoid with the test material and a step of measuring the activity of the organoid.

In the present invention, the "method of inspecting the activity or toxicity" is not limited to types thereof, and, for example, may be a contractile force-based cardiac toxicity assessment method when inspecting the activity or toxicity using a cardiac organoid.

In an embodiment of the present invention, it is desirable that the activity of the test material may be drug metabolism activity measurement or drug interaction assessment, and the activity of the test material is not limited thereto. For example, the effect of the test material on the organ may be comprehensively determined by treating the test material on a cardiac organoid and measuring changes in contractile force, beat rate, etc.

Hereinafter, the present invention will be described in more detail through Examples. These Examples are only for the purposes of illustrating the present invention, and it should be obviously construed by those skilled in the art that the scope of the present invention is not limited to these Examples.

Example 1. Preparation of Gelatin Oil Capsules 1-1. Experimental Groups 1

Microcapsules comprising gelatin, a natural polymer, and an oil were prepared by the same method as shown in FIG. 1.

Specifically, a gelatin solution was prepared by mixing 1.5 g of gelatin (pig, 300 bloom, type A) and 50 ml of deionized water, and then heating the mixture to 70° C., thereby completely melting gelatin. A natural polymer solution was prepared by mixing 1.5 g of Arabic gum and 50 ml of deionized water, and then maintaining the mixture at 70° C., thereby completely melting Arabic gum. After adding 24 g of squalane (hydrogenated poly-1-decene, Puresyn™ 4) as an oil to the gelatin solution, the squalane was stirred in the gelatin solution at a temperature of 40°° C. or more and a rotational speed of 100 to 150 rpm for five minutes by using a stirrer. After adding the natural polymer solution to the stirred gelatin solution, pH of the natural polymer solution was adjusted to a pH value of 3.1 to 3.6 in the stirred gelatin solution by an acidic solution of acetic acid or hydrochloric acid. That is, gelatin and Arabic gum were mixed at a weight ratio of 1:1. After stirring the pH-adjusted solution at a temperature of 35° C. or more for one hour, the pH-adjusted solution was cooled so that the temperature of the pH-adjusted solution became 25° C. by slowly lowering temperature of the pH-adjusted solution. Additionally, after adding water with an amount corresponding to four times the amount of the cooled solution to the cooled solution, and stirring water in the cooled solution, the stirred solution was cooled to 10° C. or less. After moving the cooled solution to a fractional funnel, gelatin oil capsules in an upper layer were separated. After adding an 0.5% glutaraldehyde aqueous solution to the separated gelatin oil capsules, the 0.5% glutaraldehyde aqueous solution was stirred in the separated gelatin oil capsules for one hour. After moving a stirred material containing the gelatin oil capsules to the fractional funnel, the stirred material containing the gelatin oil capsules was cleaned six times with deionized water. After putting completed gelatin oil capsules (gelatin: Arabic gum: hyaluronic acid=1:1:0, Experimental group 1) into deionized water, the completed gelatin oil capsules were stored in the deionized water.

1-2. Experimental Groups 2 to 4

Gelatin oil capsules were prepared by mixing gelatin, Arabic gum, and hyaluronic acid. More specifically, gelatin oil capsules of experimental groups 2 to 4 were prepared in the same method as in the Example 1-1, and natural polymer solutions prepared by mixing Arabic gum and hyaluronic acid at weight ratios of Table 1 were used.

TABLE 1

|  | Experimental group 1 | Experimental group 2 | Experimental group 3 | Experimental group 4 |
| --- | --- | --- | --- | --- |
| Gelatin | 1 | 1 | 1 | 1 |
| Arabic gum | 1 | 0.9 | 0.5 | 0.1 |
| Hyaluronic acid | 0 | 0.1 | 0.5 | 0.9 |

1-3. Experimental Groups 5 to 11

Gelatin oil capsules were prepared by adding an oil thickener, and types and concentrations of the oil thickener are shown in Table 2.

TABLE 2

| | Types of oil thickener | Concentration (%) | Temperature (° C.) |
|---|---|---|---|
| Experimental group 5 | Bentone gel ® (disteardimonium hectorite) | 10 | 80 |
| Experimental group 6 | Versagel ® ME 750 (hydrogenated polyisobutene) | 10 | 80 |
| Experimental group 7 | Rheopearl ® TT (dextrin palmitate/ ethylhexanoate) | 10 | 80 |
| Experimental group 8 | Rheopearl ® KL (dextrin palmitate) | 10 | 80 |
| Experimental group 9 | | 7 | 80 |
| Experimental group 10 | | 5 | 80 |
| Experimental group 11 | | 2 | 80 |

Specifically, a gelatin solution was prepared by mixing 3 g of gelatin (pig, 300 bloom, type A) and 100 ml of deionized water, and then heating the mixture to 70° C., thereby completely melting gelatin. A natural polymer solution was prepared by mixing 3 g of Arabic gum and 100 ml of deionized water, and then maintaining the mixture at 70° C., thereby completely melting Arabic gum. After adding oil thickeners corresponding to respective experimental groups in amounts of weight percentages (concentrations) disclosed in Table 2 along with 24.54 g of squalane (hydrogenated poly-1-decene, Puresyn™ 4) as an oil to the gelatin solution, the oil thickeners and the squalane were stirred in the gelatin solution at a temperature of 45° C. or more and a rotational speed of 100 to 150 rpm for five minutes by using a stirrer. After adding the natural polymer solution to the stirred gelatin solution, pH of the natural polymer solution was adjusted to a pH value of 3.1 to 3.6 in the stirred gelatin solution by an acidic solution of acetic acid or hydrochloric acid. After stirring the pH-adjusted solution at a temperature of 35° C. or more for one hour, the pH-adjusted solution was cooled so that the temperature of the pH-adjusted solution became 25° C. by slowly lowering temperature of the pH-adjusted solution. Additionally, after adding water with an amount corresponding to four times the amount of the cooled solution to the cooled solution, and stirring water in the cooled solution, the stirred solution was cooled to 10° C. or less. After moving the cooled solution to a fractional funnel, gelatin oil capsules in an upper layer were separated. After adding an 0.5% glutaraldehyde aqueous solution to the separated gelatin oil capsules, the 0.5% glutaraldehyde aqueous solution was stirred in the separated gelatin oil capsules for one hour. After moving a stirred material containing the gelatin oil capsules to the fractional funnel, the stirred material containing the gelatin oil capsules was cleaned six times with deionized water. After putting completed gelatin oil capsules into deionized water, the completed gelatin oil capsules were stored in the deionized water.

Example 2. Measuring Elastic Moduli of Gelatin Oil Capsules

Elastic moduli of gelatin oil capsules of the experimental groups 1 to 4 were measured. Specifically, the gelatin oil capsules were disposed between two flat plates with a radius of 20 mm in a state that the gelatin oil capsules were spaced apart from one another at intervals of 1,000 μm. The elastic moduli of the gelatin oil capsules were analyzed by fixing strain to 0.01 at room temperature, and using a rotating rheometer (TA Instruments, AR 1500ex) in a range of 0.01 to 5 Hz. Results of measuring the elastic moduli of the gelatin oil capsules are shown in FIG. 2.

As shown in FIG. 2, it is confirmed that, when preparing the gelatin oil capsules, elasticities of the gelatin oil capsules are increased in case of replacing a portion of Arabic gum with hyaluronic acid. Particularly, it is confirmed that elasticities are remarkably increased in the experimental group 3 in which Arabic gum and hyaluronic acid are mixed at a weight ratio of 1:1, and the experimental group 4 in which Arabic gum and hyaluronic acid are mixed at a weight ratio of 1:9.

Example 3. Coculturing Gelatin Oil Capsules and Cardiomyocytes

The gelatin oil capsules of the experimental group 4 prepared in Example 1 and human derived cardiomyocytes (iCell® Cardiomyocytes, CMC-100-010-001, USA, Cellular Dynamics International) were cocultured. Specifically, in order to use the gelatin oil capsules as a cell culture, the capsules were stirred in the PBS for five minutes after immersing the capsules in PBS. After finishing the stirring process, replacing the used PBS with new PBS, and additionally performing the stirring process, these processes were repeated 2 to 3 times. After finishing the stirring process, removing the PBS, and moving the gelatin oil capsules to plating mediums (plating medium 50%, Fetal Bovine Serum (FBS) (Hyclone®, SH30919.03, USA) 10%), the gelatin oil capsules were stored at 4° C. in the plating mediums for 24 hours.

In order to perform a coculturing process, cardiomyocytes were treated with trypsin and floated as single cells. After inactivating trypsin with a serum-containing medium, and centrifuging the inactivated trypsin, the cardiomyocytes were obtained. After adding a new medium to the obtained cells, and refloating the new medium-added cells, the refloated cells was counted. The counted cells were prepared so that the cells were contained in a high concentration in a medium of 200 μl. After moving the gelatin oil capsules, i.e., a cell culture to a 15 ml conical tube, a culture medium was added to the cell culture to the extent that the cell culture was wetted with the culture medium. After inoculating prepared cardiomyocytes into a conical tube containing the cell culture and the medium, the cardiomyocytes inoculated into the conical tube were cultured. The culturing process was performed overnight in an incubator maintaining a temperature of 37° C. and 5% of $CO_2$, and the incubator was tapped several times at intervals of 15 to 30 minutes so that settled cells could be floated again. After moving the culturing process completed cardiomyocyte-cell culture to a culture container with a low cell adhesive force, the cardiomyocyte-cell culture was observed by an optical microscope, a scanning electron microscope (SEM), and a transmission electron microscope (TEM). The cardiomyocyte-cell culture was observed by the same method also in the gelatin oil capsules of the experimental groups 2 to 4. Results of observing the cardiomyocyte-cell culture are shown in FIGS. 3 and 4.

As shown in FIG. 3, it is confirmed that cardiomyocytes are concentrated around gelatin oil capsules, i.e., cell cultures of the experimental groups 1 to 4. On the other hand, it is observed that cells are scattered on plates in a control group in which the cell culture is not used.

As shown in FIG. 4, it is confirmed that cardiomyocytes are adhered to the cell cultures of the experimental groups 1 to 4, and spheres are formed by the cultured cells. Particularly, it is confirmed that cardiomyocytes of the experimental groups 2 to 4 using gelatin, Arabic gum, and hyaluronic acid during the preparation of cell cultures exhibit a form similar to that of mature muscle cells.

Example 4. Analyzing Cellular Viabilities of Cocultured Cardiomyocytes

After culturing the cardiomyocytes for up to 42 days at intervals of 1 week from the 4th day of culturing so as to check viabilities of cardiomyocytes cocultured using the experimental group 4 prepared in Example 1, the viabilities of the cardiomyocytes were checked through live-dead assay (abcam, ab65470). After performing the live-dead assay in accordance with the manual of a manufacturer, results of the assay are shown in FIG. 5.

As shown in FIG. 5, green fluorescence refers to live cells, red fluorescence refers to dead cells, and it is confirmed that most cells are alive regardless of the number of inoculated cells or the period of culturing.

Example 5. Coculturing Gelatin Oil Capsules and Cardiomyocytes Differentiated from Mesenchymal Stem Cells Gelatin oil capsules comprising an oil thickener of the experimental group 10 prepared in Example 1 and cardiomyocytes (FUJIFILM, Cellular Dynamics International, iCell® Cardiomyocytes) were cocultured. Specifically, in order to use the gelatin oil capsules as a cell culture, the capsules were stirred in the PBS for five minutes after immersing the capsules in PBS. After finishing the stirring process, replacing the used PBS with new PBS, and additionally performing the stirring process, these processes were repeated 2 to 3 times. After finishing the stirring process, removing the PBS, and moving the gelatin oil capsules to plating mediums (plating medium 50%, Fetal Bovine Serum (FBS) (Hyclone®, SH30919.03, USA) 10%), the gelatin oil capsules were stored at 4° C. in the plating mediums for 24 hours.

After inoculating cardiomyocytes into a conical tube containing the cell culture and the medium, the cardiomyocytes inoculated into the conical tube were cultured. The culturing process was performed overnight in an incubator maintaining a temperature of 37° C. and 5% of $CO_2$. In order to check whether or not the inoculated cells were evenly applied to the surface of the cell culture, the cardiomyocytes were dyed with DiI and DiD, seeded twice, and then observed by a confocal microscope. Results of the observation are shown in FIG. 6.

As shown in FIG. 6, it is confirmed that the cardiomyocytes are evenly well adhered to the entire surface of the gelatin oil capsules comprising Rheopearl® KL (Dextrin Palmitate) as an oil thickener of the experimental group 10, without any gaps therebetween.

Example 6. Coculturing Gelatin Oil Capsules and Cervical Carcinoma Cells

Gelatin oil capsules comprising an oil thickener of the experimental group 10 prepared in Example 1 and HeLa cells (ATCC) were cocultured. The experimental process was performed in the same manner as in Example 3. After observing the cells by a microscope in two days after cell adhesion, observation results are shown in FIG. 7.

As shown in FIG. 7, it is confirmed that the HeLa cells are normally adhered to gelatin oil capsules comprising Rheopearl® KL as an oil thickener of the experimental group 10.

It may be confirmed through the above-mentioned experiments that gelatin oil capsules comprising an oil thickener according to the present invention may be used as a carrier for culturing various cells.

Example 7. Observing Cocultured Cardiomyocytes Using a Transmission Electron Microscope Cardiomyocytes cocultured with the experimental group 4 prepared in Example 1 were observed by using a transmission electron microscope (TEM). Specifically, cardiomyocytes were cocultured and prepared by the same method as in Example 3-1 in experimental groups, and the cardiomyocytes were cocultured by a conventionally known method in the control group. After observing the cultured cardiomyocytes by the TEM, results of the observation are shown in FIGS. 8 and 9.

As shown in FIGS. 8 and 9, a plurality of immature cardiomyocytes are observed in the control group. On the other hand, a plurality of mature muscle cells are observed in the experimental groups, and it is confirmed that spheres similar to the structure of the heart with ventricular structure are formed by the cultured cells. As it is confirmed from the foregoing results that using gelatin oil capsules as a cell culture not only forms the spheres similar to the structure of the heart with ventricular structure, but also matures the cardiomyocytes, a structure in which the cardiomyocytes are cultured in the gelatin oil capsules may be used as an artificial myocardial structure, i.e., an organoid.

Next, the cocultured cardiomyocytes were observed by the TEM so as to check the maturation degree of intracellular organelles of the cocultured cardiomyocytes. Specifically, the cocultured cardiomyocytes were immobilized in a low temperature environment of 4° C. by using 2.5% glutaraldehyde in PBS. The immobilized cells were washed with a 0.1 M phosphate buffer solution with a pH value of 7.4 for 10 to 20 minutes. A postprocess included carrying out a reaction process using 1% $OsO_4$ (osmic acid) for about one hour, and performing a washing process again by using the 0.1 M phosphate buffer solution with a pH value of 7.4. In order to remove moisture within samples, 50%, 70%, 80%, 95%, and 100% ethyl alcohols were dehydrated from low concentrations to high concentrations within five minutes. After cutting the samples to 1 μm by using an ultramicrotome, and moving the cut samples to slide glasses, the cut samples were adhered and fixated to the hot plates while extending the samples on hot plates with a temperature of 80° C. After passing the samples adhered and fixated to the hot plates through an electron staining process, and observing the samples passing through the electron staining process, results of the observation are shown in FIG. 9.

As shown in FIG. 9, some myofibrils and mitochondria are observed in two weeks after performing the culturing process, and mature mitochondria and myofibrils are observed from the fifth week compared to the second week. Furthermore, it is confirmed that polynucleated cells and solid junction that may be seen from mature cardiomyocytes are formed.

Example 8. Comparing Properties of Gelatin Oil Capsules Depending on the Addition of an Oil Thickener After comparing viscosities, forms, and whether or not to form an emulsion of gelatin oil capsules of the experimental groups 5 to 11, comparison results are shown in Table 3.

TABLE 3

| | Viscosity (at room temperature) | Form | Emulsion formation | Others |
|---|---|---|---|---|
| Experimental group 5 | Low | Particles are formed, and have dull brown color | — | The viscosity is very low |
| Experimental group 6 | Low | Transparent | — | |
| Experimental group 7 | High | Formation of a gel that is dull and thixotropic | — | |
| Experimental group 8 | Very high | Formation of a gel that is dull and hard | — | The viscosity is very high |
| Experimental group 9 | High | Formation of a gel that is dull and hard | Nonexistence | The emulsion formation efficiency is low |
| Experimental group 10 | High | Formation of a gel that is dull and hard | Existence | Appropriate |
| Experimental group 11 | Low | Formation of a gel that is dull and hard | Existence | The viscosity enhancement effect is low |

As shown in Table 3, it may be seen that properties of the gelatin oil capsules are changed depending on the addition of an oil thickener. Particularly, it may be seen that the gelatin oil capsules of the experimental group 10 using Rheopearl® KL (Dextrin Palmitate) with 5% concentration as the oil thickener have a high viscosity at room temperature, not only form a gel that is dull and hard, but also form an emulsion.

Example 9. Comparing Retention Degrees of Gelatin Oil Capsules Depending on Whether or not to Add an Oil Thickener A retention degree of gelatin oil capsules of the experimental group 4 to which an oil thickener was not added under physical conditions and that of gelatin oil capsules of the experimental group 10 to which the oil thickener was added were compared. Specifically, a partial pressure was applied to each of the foregoing gelatin oil capsules by using a needle. Retention degrees of the pressure-applied gelatin oil capsules were observed. Results of comparing the retention degrees of the gelatin oil capsules are shown in FIG. 10.

As shown in FIG. 10, it is confirmed that, although a partial pressure is applied to the gelatin oil capsules of the experimental group 10 to which the oil thickener is added, the gelatin oil capsules of the experimental group 10 are not burst while maintaining the smooth state. Moreover, it is confirmed that the gelatin oil capsules of the experimental group 10 to which the oil thickener is added maintain their shapes without spreading oil inside the gelatin oil capsules even after the gelatin oil capsules are burst by continuous stimulation. On the other hand, it may be seen that the gelatin oil capsules of the experimental group 4 to which an oil thickener is not added are burst due to the pressure applied thereto, and it is confirmed that oil inside the gelatin oil capsules is flown out and spread. The foregoing results mean that adding the oil thickener during the preparation of the gelatin oil capsules improves the retention degree of prepared capsules. Furthermore, as oil inside oil thickener-added gelatin oil capsules maintains its form even after the capsules are burst, it may be seen that oxygen may be continuously supplied to the cells under culturing although the gelatin oil capsules are damaged when culturing cells by using the oil thickener-added gelatin oil capsules.

Example 10. Checking Beat Rate and Beating Intervals of an Artificial Myocardial Structure It was confirmed that the cells were matured when coculturing gelatin oil capsules and cardiomyocytes, and it was confirmed that cardiomyocytes forming spheres could be used as an artificial myocardial structure. So as to prove that cultured cardiomyocytes could be used as the artificial myocardial structure, beat rate and beating intervals of cardiomyocytes that had been cocultured using the experimental group 4 prepared in Example 1 were checked. Specifically, beat rates and beating intervals per minute of the artificial myocardial structure were measured at intervals of one week from day 4 of culturing up to day 42 of culturing through video shooting. Results of checking the beat rates and the beating intervals are shown in FIG. 11.

As shown in FIG. 11, it may be confirmed that, although the beating intervals, as beating intervals between 2 seconds and 4 seconds, are somewhat irregular, and beat rates are also slow in the early stage of culturing, the beating intervals become regular from the 21st day after culturing.

Next, after culturing cardiomyocytes in the same manner by using gelatin oil capsules comprising an oil thickener of the experimental group 10 prepared in Example 1, whether the cultured cardiomyocytes were beating or not was checked. The checking results are shown in FIG. 12.

As shown in FIG. 12, as results of checking beats of the cardiomyocytes on the 21st and 43rd days of culturing, it is confirmed that beating intervals are shown to be regular and stable. Particularly, although there is a case that gelatin capsules burst in the middle of the experiment (a yield of about 35% on the 43rd day of culturing) when the oil thickener is not included, it is confirmed that gelatin oil capsules comprising an oil thickener according to the present invention are stably maintained without a bursting phenomenon being found until the 43rd day of culturing.

Example 11. Production and Functional Verification of a Cardiac Organoid 11-1. Production of a Cardiac Organoid A cardiac organoid was produced by coculturing gelatin oil capsules containing gelatin, a natural polymer, an oil, and an oil thickener according to the present invention established through the aforementioned experimental processes and human derived cardiomyocytes (iCell® Cardiomyocytes, CMC-100-010-001, USA, Cellular Dynamics International). Specifically, in order to use the gelatin oil capsules as a cell culture, the capsules were stirred in the PBS for five minutes after immersing the capsules in PBS. After finishing the stirring process, replacing the used PBS with new PBS, and additionally performing the stirring process, these processes were repeated 2 to 3 times. After finishing the stirring process, removing the PBS, and moving the gelatin oil capsules to plating mediums (plating medium 50%, Fetal Bovine Serum (FBS) (Hyclone®, SH30919.03, USA) 10%), the gelatin oil capsules were stored at 4° C. in the plating mediums for 24 hours.

In order to perform a coculturing process, cardiomyocytes were treated with trypsin and floated as single cells. After inactivating trypsin with a serum-containing medium, and centrifuging the inactivated trypsin, the cardiomyocytes were obtained. After adding a new medium to the obtained cells, and refloating the new medium added cells, the refloated cells was counted. The counted cells were prepared so that the cells were contained in a high concentration in a medium of 200 µl. After moving the gelatin oil capsules, i.e., cell culture to a 15 ml conical tube, a culture medium was added to the cell culture to the extent that the cell culture was wetted with the culture medium. After inoculating prepared cardiomyocytes into a conical tube containing the cell culture and the medium, the cardiomyocytes inoculated into the conical tube were cultured. The culturing process was performed overnight in an incubator maintaining a temperature of 37° C. and 5% of $CO_2$, and the incubator was tapped several times at intervals of 15 to 30 minutes so that settled cells could be floated again, thereby enabling the cells to be evenly adhered to the gelatin oil capsules. A cardiac organoid was established by culturing the cardiomyocyte-adhered gelatin oil capsules at a temperature of 37° C. and in a 5% $CO_2$ culturing environment for 5 weeks.

11-2. Functional Verification of a Cardiac Organoid

Maximum depolarization velocity ($V_{max}$), beat rate, repolarization time (APD90), and maximum voltage level (total amplitude) were checked to verify functions of a cardiac organoid (an artificial myocardial structure) produced through the aforementioned processes.

Specifically, the electrophysiological maturity of hiPSC-CM according to a 2D or gelatin oil capsule culturing environment was analyzed by a patch clamp method. In order to perform a patch clamp recording process, after moving a hiPSC-CM cultured in the 2D or gelatin oil capsule (cardiac organoid) culturing environment for 1, 3, and 5 weeks to 16 mm cover glasses, maintaining the hiPSC-CM moved to the cover glasses for 2 to 3 days, and moving the hiPSC-CM to a recording chamber for patch clamp that was installed on an inverted microscope, action voltages were measured. The action voltage measuring process comprised closely adhering a glass microelectrode with a resistance of 2 to 3 MΩ to a cellular membrane, measuring action voltages under whole-cell recording conditions (conventional whole-cell patch configuration), and selecting cells showing voluntary contraction in an environment maintaining a physiological temperature (37° C.). A composition for chamber solution and a composition for glass microelectrode solution used in recording the action voltages are as follows.

The chamber solution is corrected by 3.5 mM KCl, 10 mM HEPES, 145 mM NaCl, 1 mM $MgCl_2$, 1.8 mM $CaCl_2$, 5 mM glucose, and pH 7.4 NaOH.

The glass microelectrode solution is corrected by 25 mM KCl, 120 mM K-aspartate, 5 mM NaCl, 10 mM HEPES, 0.1 mM EGTA, 1 mM $MgCl_2$, 3 mM MgATP, and pH 7.2 KOH.

Action voltages were recorded by using a patch clamp amplifier (Axopatch 1D, Axon Instrument, Inc., Ca, USA), an analog-digital converter (Digidata-1550, Axon Instrument, Inc.), and a pClamp 11 (Axon Instrument, Inc.) program. After analyzing the maximum depolarization velocity ($V_{max}$), beat rate, repolarization time (APD90), and maximum voltage level (total amplitude) as action voltage properties by using a Clampfit 11 (Axon Instrument, Inc.) program, analysis results are shown in FIG. 13. Results of additionally analyzing the beat rate and the repolarization time are shown in FIG. 14.

As shown in FIG. 13, it may be seen that the cardiomyocytes cultured along with gelatin oil capsules according to the present invention have a low and even maximum depolarization velocity ($V_{max}$) compared to cells cultured by a conventional 2D method. Moreover, it may be seen that the cells are matured when checking the beat rate, repolarization time, and maximum voltage level (total amplitude) of the cardiomyocytes cultured along with the gelatin oil capsules according to the present invention.

As shown in FIG. 14, the cardiomyocytes cultured along with gelatin oil capsules according to the present invention have a short repolarization time and an uneven beat rate in one week after culturing, but have increased beat rate and repolarization time in three weeks after culturing. In contrast, it is confirmed that cells cultured by the conventional 2D method are found to have little change in one week and three weeks after starting the culturing process. The foregoing results mean that cultured cardiomyocytes are matured when culturing the cardiomyocytes along with gelatin oil capsules according to the present invention. Therefore, as cells forming an artificial myocardial structure prepared by coculturing the cardiomyocytes using the gelatin oil capsules each have similar beat rate and repolarization time, it may be seen that the artificial myocardial structure are actually very similar to a myocardial structure, and may function as a cardiac organoid.

Furthermore, after additionally treating an artificial myocardial structure prepared by coculturing gelatin oil capsules and cardiomyocytes with various drugs, contractile forces of the drug-treated artificial myocardial structure were checked. The checking results are shown in FIG. 15.

As shown in FIG. 15, it may be confirmed that, as results of observing beat rates under drug reaction conditions, beat rates slow down and become somewhat irregular in a group treated with 125 nM verapamil, and it is observed that the beat rates are accelerated, and contractile forces are changed strongly in a group treated with 10 nM Isopreterenol. Furthermore, it is confirmed that the beat rates are changed into slow beat rates, and the contractile forces are also weakened in a group treated with 100 nM Nifedipine. It is confirmed through this that a more accurate cardiotoxicity response of drug may be predicted as a response such as the drug effect exhibiting in humans may be measured even in an artificial myocardial structure (cardiac organoid) according to the present invention that has been artificially prepared.

Example 12. Preparing Artificial Cell Structures by Using Various Cells

Artificial cell structures were prepared by coculturing gelatin oil capsules and various cells. More specifically, respective artificial cell structures were prepared by using Rat neonatal cardiomyocytes, human adipose-derived stem cells, human cord blood-derived endothelial progenitor cells, and Rabbit chondrocytes. The prepared artificial cell structures of Rat neonatal cardiomyocytes, human adipose-derived stem cells, and human cord blood-derived endothelial progenitor cells were observed by a TEM, and the artificial cell structure of Rabbit chondrocytes was observed through immunohistochemical staining. The prepared artificial cell structures are shown in FIG. 16.

As shown in FIG. 16, it is confirmed that all of Rat neonatal cardiomyocytes, human adipose-derived stem cells, human cord blood-derived endothelial progenitor cells, and Rabbit chondrocytes are adhered to gelatin oil capsules, are cultured on the gelatin oil capsules, and finally form spherical artificial cell structures.

Overall, the present inventors have confirmed that the cells are matured when culturing microcapsules according to the present invention and cells together with the capsules, and an organoid produced using the cells cultured along with the microcapsules, when treated with a drug, reacts to the toxicity of the drug. Therefore, an organoid according to the present invention may be diversely used in the development of new drugs, disease research, and the field of artificial organ development.

The invention claimed is:

1. A method for organoid production, comprising co-culturing mammalian cells and a carrier for three-dimensional (3D) mammalian cell culture, the carrier comprising microcapsules each having a wall containing gelatin and a natural polymer, surrounding a core containing an oil, and dextrin palmitate as an oil thickener, to produce organoids, wherein
the natural polymer is one or more selected from the group consisting of Arabic gum, hyaluronic acid, guar gum, pectin, xanthan gum, locust bean gum, tamarind gum, tragacanth gum, gum ghatti, locust bean gum, Konjac gum, agar, Carragheenan, furcellaran, and gellan, and wherein
the oil is one or more selected from the group consisting of olive oil, camellia oil, castor oil, palm oil, Jojoba oil, almond oil, grapeseed oil, herbal oil, rose oil, coconut oil, moringa oil, rice bran oil, apricot kernel oil, sunflower oil, meadowfoam seed oil, Abyssinian oil, and squalane.

2. The method of claim 1, wherein the microcapsules are prepared by mixing the gelatin and the natural polymer at a weight ratio of 1:0.1 to 1.

3. The method of claim 2, wherein the natural polymer is a mixture of Arabic gum and hyaluronic acid.

4. The method of claim 3, wherein the Arabic gum and hyaluronic acid are mixed at a weight ratio of 1:9 to 9:1.

5. The method of claim 1, wherein the oil thickener is contained in an amount of 1 to 15 wt % with respect to the weight of the oil.

6. The method of claim 1, wherein the mammalian cells are anchorage-dependent cells.

7. The method of claim 6, wherein the anchorage-dependent cells are one or more selected from the group consisting of cardiomyocytes, vascular endothelial cells, lipocytes, epithelial cells, fibroblasts, osteoblasts, chondrocytes, hepatocytes, uterine cervical cells, cancer cells, and mesenchymal stem cells.

* * * * *